US011541138B2

(12) United States Patent
Willocx et al.

(10) Patent No.: US 11,541,138 B2
(45) Date of Patent: Jan. 3, 2023

(54) METHOD FOR CLEANING SURFACES IN INTERIOR SPACES AND IN TECHNICAL EQUIPMENTS WITH BENIGN BACTERIA

(71) Applicant: LIVING TECHNOLOGIES, COOPERATIVE VENNOOTSCHAP MET BEPERKTE AANSPRAKELIJKHEID, Opwijk (BE)

(72) Inventors: Filip Willem Maria Willocx, Heverlee (BE); Koen De Koster, Opwijk (BE)

(73) Assignee: LIVING TECHNOLOGIES, COOPERATIVE VENNOOTSCHAP MET BEPERKTE AANSPRAKELIJKHEID, Opwijk (BE)

( * ) Notice: Subject to any disclaimer, the term of this patent is extended or adjusted under 35 U.S.C. 154(b) by 525 days.

(21) Appl. No.: 16/479,681

(22) PCT Filed: Jan. 24, 2018

(86) PCT No.: PCT/IB2018/050424

§ 371 (c)(1),
(2) Date: Jul. 22, 2019

(87) PCT Pub. No.: WO2018/138645

PCT Pub. Date: Aug. 2, 2018

(65) Prior Publication Data

US 2021/0322610 A1 Oct. 21, 2021

(51) Int. Cl.

*A61L 9/00* (2006.01)
*A62B 7/08* (2006.01)

(Continued)

(52) U.S. Cl.

CPC ................ *A61L 2/22* (2013.01); *A01N 25/06* (2013.01); *A01N 63/20* (2020.01); *A01N 63/22* (2020.01);

(Continued)

(58) Field of Classification Search

CPC ........ A61L 2/0082; A61L 2/0094; A61L 2/20; A61L 2/22; A61L 2202/25

(Continued)

(56) References Cited

FOREIGN PATENT DOCUMENTS

| | | | | |
|---|---|---|---|---|
| BE | 2 329 893 A1 | | 7/2011 | |
| BE | 2 329 893 B1 | * | 7/2016 | ............... A61L 9/14 |

(Continued)

OTHER PUBLICATIONS

T. Nishihara et. al., Studies on the Bacteria Spore Coat, Microbiol. Immunol., Jun. 4, 1981, No. 25(8), pp. 763 to 771 (D10).

*Primary Examiner* — Monzer R Chorbaji
(74) *Attorney, Agent, or Firm* — John Alumit

(57) ABSTRACT

Method that allows surfaces in interior spaces or technical equipments to be cleaned, characterised in that it comprises at least the following step: —the targeted atomization on the surfaces of a liquid with spores of benign bacteria on all or certain types of surfaces by means of an electrically and/or pneumatically powered atomizer, while the space remains accessible to people and animals, with the purpose of speeding up the cleaning of interior spaces and of technical equipments, lowering the cleaning frequency, and lowering the dust deposit.

15 Claims, 3 Drawing Sheets

(51) Int. Cl.

| | |
|---|---|
| ***A61L 2/22*** | (2006.01) |
| ***A01N 63/20*** | (2020.01) |
| ***A01N 63/22*** | (2020.01) |
| ***A01N 63/25*** | (2020.01) |
| ***A01N 25/06*** | (2006.01) |
| ***B08B 9/00*** | (2006.01) |
| ***B08B 17/02*** | (2006.01) |
| *A61L 101/32* | (2006.01) |

(52) U.S. Cl.
CPC ................ *A01N 63/25* (2020.01); *B08B 9/00* (2013.01); *B08B 17/02* (2013.01); *A61L 2101/32* (2020.08); *A61L 2202/17* (2013.01); *A61L 2202/25* (2013.01)

(58) Field of Classification Search
USPC ........................................... 422/28, 120, 123
See application file for complete search history.

(56) References Cited

FOREIGN PATENT DOCUMENTS

| | | | | |
|---|---|---|---|---|
| EP | 2 329 893 A1 | | 6/2011 | |
| JP | 2000-503320 | | 3/2000 | |
| JP | 2003-157500 | | 5/2003 | |
| JP | 2004-351321 | | 12/2004 | |
| JP | 2007-522264 | | 8/2007 | |
| JP | 3161025 | | 7/2010 | |
| JP | 2010-274249 | | 12/2010 | |
| JP | 2015-523991 | | 8/2015 | |
| JP | 2016-153508 | | 8/2016 | |
| JP | 2017-006341 | | 1/2017 | |
| WO | WO2006/125283 A1 | | 11/2006 | |
| WO | WO-2006125283 A1 | * | 11/2006 | ............ A01N 63/00 |

* cited by examiner

METHOD FOR CLEANING SURFACES IN INTERIOR SPACES AND IN TECHNICAL EQUIPMENTS WITH BENIGN BACTERIA

The present invention relates to a method for cleaning surfaces in interior spaces and in technical equipment.

In particular, the invention is intended for the more efficient visual cleaning and slowing down of dust deposit for all types of surfaces in an interior space or in technical equipment.

It is known that cleaning surfaces in an interior space is a labour-intensive activity nowadays. In every house, building or production space, in every transport means and in all industrial and technical equipment all types of surfaces need to be cleaned periodically, and this both in case of normal use and after incidents such as fire or water damage.

Traditionally a cleaning company or the tenant or owner of a building establishes a regular cleaning programme whereby the surfaces in the interior spaces to be cleaned are described and whereby the frequency of cleaning and the cleaning products to be used are determined.

A specific cleaning programme is usually developed for all possible interior spaces of the building.

For residential buildings these are living rooms, bedrooms, bathrooms, kitchens, sanitary facilities such as showers and toilets, storage areas such as attics and cellars, stairwells and corridors, elevators and garages for vehicles and garden houses.

For industrial buildings or educational institutes these are reception areas, production halls, laboratories, training centres, classrooms, workplaces, dressing rooms, desks and offices, gym areas, sports centres, sanitary facilities such as showers and toilets, conference rooms, stairwells and corridors, elevators, storage areas, canteens, eating areas and restaurants, garages for company vehicles and the like.

For buildings intended for medical care or support to people in need such as hospitals, rehab centres, care homes or therapeutic institutions these are reception areas, waiting rooms, desks and offices, operating theatres, consultation rooms, spaces with diagnostic equipment, sanitary facilities for care, patient rooms, kitchens and canteens, eating areas and restaurants, garages for ambulances and patient transport, stairs, corridors and elevators, supply rooms, pharmacy rooms and the like.

Interior spaces of means of transport such as aircraft, cruise ships, cars, buses, trains and trams also need to be regularly cleaned.

In addition to the accommodation spaces, spaces that are difficult to access for manual cleaning also need to be regularly cleaned such as in technical equipment[[s]] and air treatment systems, air ducts, heating installations, elevator shafts and elevator cages, technical shafts and areas, pipes behind false ceilings or in cooling floors in data centres for computers and servers, cellars and crawl spaces, cinema and theatre auditoriums, high stairwells, inner courts, etc.

Each room has different types of surfaces which often need to be cleaned with a specific cleaning product and a specific technique: stone and wooden floors, carpets, walls, doors and ceilings, cupboards, glass and mirrors, windowsills, surfaces of a desk, chairs and tables, lamps, settees, beds, telephones, computers, televisions, books, paintings, art objects, plants, sunblinds and louvres, curtains—the list is pretty endless.

The frequency of cleaning is determined by the average level of soiling and the desired cleaning quality of the building as a function of the predetermined budget. Because of the many working hours required on a day-to-day basis to keep all kinds of surfaces in interior spaces clean, the cleaning activity becomes very expensive.

The following list indicates the biggest problems for the cleaning companies in a work environment:

i) Budgets and costs for cleaning are too high: the manual work covers at least 80% of the costs charged to the customer;

ii) bad or insufficient visual quality of the result;

iii) health problems in the building due to chemical pollution;

iv) odour nuisance in the building (toilets, perspiration, carpets);

v) non-sustainable cleaning, use of corrosive and toxic chemicals;

vi) health and safety problems for the cleaners: accidents, long-term absences;

vii) lack of organised communication between customer and cleaning company.

The cleaning sector has been going through a constant rationalisation since the eighties with the aim of improving productivity and reducing costs. A large number of companies, including many small and medium-sized enterprises is under constant competitive pressure.

As approximately 80% of the costs charged to the customers are labour costs, cost cuts often mean reducing personnel, increasing work load, such that health and safety standards slip. Some companies do not respect the labour laws and push the prices downwards. The pressure on the companies has a counterproductive effect on the quality of the services, which in the longer term may endanger the sector's income.

According to Dr. Herbert Sinner (Henkel, 1959, "Uber das Waschen mit Haushaltwaschmaschinen", Haus+Heim-Verlag), the cleaning process is influenced by four factors that have an influence on each other:

a) a chemical reaction due to the operation of the cleaning product, b) at a certain temperature, c) during a certain contact time on the dirt, and d) a mechanical treatment by means of a brush or microfibre cloth.

When one factor is reduced or removed it needs to be compensated by one or several of the other factors.

For instance, you can opt to use less strong chemicals, but then it needs to be compensated by a longer contact time or higher temperature.

Many solutions are offered to reduce the total time required for the cleaning: solutions to limit the preparation time, or the application of the cleaning product, shortening the contact time and the treatment time of the surface, rinsing and drying surfaces sooner and clearing up the tools more quickly.

Examples of solutions whereby less working hours are needed to clean surfaces comprise the use of microfibre cloths and mops, limiting the cleaning to the places where needed, not using too many different cleaning products, cleaning with two hands at the same time, not dosing the cleaning products manually, not using too much water such that limescale is avoided and the surfaces don't stay wet too long, and automated cleaning by scrubbing machines.

However, these solutions are limited because there is no universal method that can be used on all surfaces, because the cleaning products leave residues and too much water or because no solution is offered for surfaces that are difficult to reach manually. Ultimately, the cleaning frequency remains the same.

WO 2006/125283 A1 describes a method for keeping surfaces free from pathogenic bacteria by applying non-pathogenic bacteria including *Bacillus* varieties.

BE 1018722 A5 describes a device to atomize non-pathogenic bacteria of the genus *Bacillus* on a pet and its surrounding to block pathogenic bacteria.

In EP 2329893 B1 of Metatecta a method is presented for the microbiological cleaning of an interior space. The method comprises a two-step technique in an enclosed space, whereby first a biocide is atomized and one hour later a mixture of spores of aerobic spore forming *Bacillus* varieties. This method describes a method to sanitise an interior space biologically contaminated by viruses bacteria, spores, yeasts or moulds. In this method no people or animals are permitted in the space during the treatment.

In EP 2863959 A2 of Living Technologies a method is presented for removing particulate matter smaller than 10 μm in indoor environments. The method comprises the atomization in an enclosed space of a mixture of spores of bacteria to metabolize the particles. In this method no people or animals are permitted in the space during the treatment either.

In both aforementioned methods non-targeted atomized droplets are used, with the aim of slowly letting the droplets descend through the air in the spaces to be cleaned, which raises the treatment duration per space.

The purpose of the present invention is to provide a solution to the aforementioned limitations and other disadvantages, by providing a method that allows surfaces in interior spaces to be cleaned more quickly, consisting of at least the following step:

- the targeted atomization on the surfaces of a liquid with spores of benign bacteria on all or certain types of surfaces by means of an electrical and/or pneumatically powered atomizer, while the space remains accessible to people and animals, with the purpose of speeding up the cleaning of interior spaces and of technical equipment, lowering the cleaning frequency, and lowering the dust deposit.

An advantage connected to this method is that it allows the surfaces to be cleaned to be moistened very quickly and in a targeted way whereby the surfaces that were sprayed don't feel wet, but are covered in benign bacteria.

An added advantage of this method is that no detergents or cleaning chemicals are required anymore and manipulations such as dissolving in water and pouring out buckets are no longer necessary.

Preferably the electrical and/or pneumatic atomizer atomizes the liquid with spores of benign bacteria to a droplet size that is smaller or equal to 80 μm, whereby the treated surfaces feel moist, but don't look wet.

Preferably the concentration of spores of benign bacteria in the liquid to be atomized amounts to between $10^6$ KVE/ml and $50\times10^7$ KVE/ml, whereby sufficient benign bacteria are applied on the parts of the surface covered by the atomization.

Preferably the electrical or pneumatic atomizer is an ultra-low volume atomizer, which generates a straight jet with a reach up to 15 metres or less.

An example of such an atomizer is the targeted Vectornate atomizer type C20 or DC20. This straight jet allows to obtain a cleaning of the surface, also in spaces that are difficult to access for manual cleaning.

Preferably the electrical atomizer atomizes the liquid with spores of benign bacteria at a flow rate of maximum 300 ml per minute and at an air flow of 0.2 litre a minute on the surface at a pressure of maximum 18 KPa.

An advantage of such atomization is that a good distribution over the surface is obtained, without the surface feeling wet.

Optionally this step is followed by

- the manual or mechanical cleaning of the surfaces by means of a microfibre cloth.

An advantage of this manual cleaning with a microfibre cloth is that this step can also be done quickly, as the microfibre does not have to be moistened, and the treated surfaces do not have to be covered or treated with aqueous solutions with detergents for example.

Preferably the quantity of atomized liquid with spores of benign bacteria, applied per square metre of treated surface, amounts to maximum 10 grammes per $m^2$.

An advantage of these quantities is that they are much smaller than with a conventional wet cleaning of surfaces such as for floors, such that they are not only much quicker to apply, but also don't make the surface feel wet.

The atomized spores of bacteria in the atomized liquid are preferably chosen from the spores of benign bacteria of the genus *Bacillus* for applications at room temperature, and preferably comprise *Bacillus subtilis, Bacillus amyloliquefaciens, Bacillus pumilus, Bacillus licheniformis* or *Bacillus megaterium* or a combination of two or more of these strains.

For applications in cold environmental temperatures between 4 and 18° C. the spores of benign bacteria in the atomized liquid are preferably chosen from the spores of aerobic spore forming cold-tolerant bacteria of the genera Sporosarcina, Paenisporosarcina, or *Paenibacillus* or comprise a combination thereof and for the genus Sporosarcina globispora, *aquimarina*, or *psychrophila* or a combination of two or more of these strains.

For the genus Paenisporosarcina the atomized liquid preferably contains spores of Paenisporosarcina macmoerdoensis, and for the genus *Paenibacillus* preferably spores of *Paenibacillus glacialis, amylolyticus, pabuli*, xylanexedens, castaneae, or *macquariensis antarcticus* or a combination of two or more of these strains.

An advantage of these cold-tolerant bacteria is that they also thrive at lower temperatures.

When using an electrical and/or pneumatic atomizer a liquid with benign bacteria is atomized with a droplet size smaller than or equal to 80 μm. The amount of liquid can be restricted to maximum 10 grammes per $m^2$ such that the surface does not feel wet and there is no danger for slipping and no stripes or streaks are visible when people, animals or trolleys step or roll over the wet floors.

An advantage of this method is that the time of the cleaning of the surfaces can be reduced by 20 to 30%.

In a preferred embodiment a solution of spores of aerobic spore-forming *Bacillus* varieties dissolved in demineralised water with 1% isopropyl-alcohol or another suitable alcohol is atomized.

The aim of adding an alcohol is to degrease the surfaces in combination with the use of a microfibre.

During a test period of two months for the cleaning of sanitary facilities, this solution was atomized on all surfaces that needed to be cleaned. The atomization was done with a targeted Vectornate atomizer type C20.

The time savings with this method in relation to the traditional method for cleaning the sanitary facility amounted to 30%.

For the cleaning of stairwells and hotel rooms the time savings with this method in relation to the traditional method amounted to 20%.

For the cleaning of fitting rooms of shops this method in relation to the traditional method resulted in a substantially reduced amount of visual dust after a fixed time interval, such that the cleaning frequency could be lowered.

In the table I below a number of measurement data is provided whereby the required time and the dust load after cleaning was measured and a comparison was made between the conventional cleaning method with detergents and water versus the method according to the invention.

The table compares the method according to the invention with the conventional method and this for three different environments. The required time was measured every time and also the dust load of the surfaces before, during and after cleaning, and again one week later (after 7 days).

The table shows that the time for cleaning is significantly shorter with the method according to the invention, and also that the obtained results strongly reduce the dust load afterwards.

TABLE I

Comparison of the method according to the invention with the conventional method for cleaning three different environments.

| Method | steps | product | Time min | Dust load g/$m^2$ BEFORE | AFTER | AFTER 7 d |
|---|---|---|---|---|---|---|
| 1 - Showroom of 400 $m^2$ with furniture | | | | | | |
| Invention | Atomize + microfibre cloth | Spores-mixture | 27 | 12.3 | 3.07 | 4.72 |
| Conventional | Deterg. Mixture + cloth | detergent | 39 | 12.3 | 8.78 | 10.45 |
| 2 - Air box section 42 $m^2$ panels with insulating material | | | | | | |
| Invention | Atomize + microfibre cloth | Spores-mixture | 14 | 22.4 | 7.57 | 8.89 |
| Conventional | Deterg. Mixture + cloth | detergent | 19.4 | 22.4 | 8.78 | 14.59 |
| 3 - Computer room 84 $m^2$ with tables, chairs and computers | | | | | | |
| Invention | Atomize + microfibre cloth | Spores-mixture | 17 | 8.3 | 3.23 | 3.99 |
| Conventional | Deterg. Mixture + cloth | detergent | 25 | 8.3 | 5.67 | 6.81 |

In the first environment, the showroom of 400 $m^2$ with furniture, the method according to the invention results in time savings of 30% in relation to the conventional method. It is possible to work faster in large store areas, where many different objects are located closely against each other which in turn consist of separate components (textiles, glass, wood, metal) which conventionally are cleaned with specific means.

With the method according to the invention only one product is used for all types of objects, more specifically the atomized spore mixture of benign bacteria. The atomized jet of the electric atomizer has a greater reach than a human action and can also penetrate much easier under, between and above all objects.

In a second environment, an air box section with panels with insulating material, an air box needs to be cleaned, in which outside air is sucked in, and is then heated and/or cooled and humidified, before being distributed in a building. Such an air box is characterised by a series of metal parts and insulating materials which are difficult to access manually, which collect a lot of dust and dirt. The fine atomized jet of the electrical atomizer allows the jet to be targeted on these components and to get to the dirty parts which before were not or barely accessible for cleaning.

With the method according to the invention the required time is less, and there is less dust accumulation in corners and sides.

In a third environment, a computer room with tables, chairs and computers as can be found in training centres, there were also considerable time savings when cleaning the room with the method according to the invention. The electric atomizer allows a fine atomized jet to be targeted on legs of chairs, computer screens, electric cables and computer screens, as well as in the areas between and under the computers, where a lot of dust particles tend to stick to.

Here too, the method according to the invention allows a reduction of dust accumulation and a lowering of the frequency of cleaning, without compromising the proper operation of the computers.

One of the technical solutions to control the climate in an indoor environment is the installation of a cooling ceiling or a climate ceiling. An important disadvantage of this technique is that on top of the climate ceiling the air has to circulate and an enormous amount of visual dirt occurs. At worst, entire dust clouds fall down in case of large air flows. The gap above the climate ceiling is very restricted, to a couple of centimetres, making it impossible to manually clean it directly.

A comparison was made between the cleaning of the gap above the climate ceiling with the conventional method, i.e. the use of a vacuum cleaner, and the method according to the invention, whereby a targeted jet of atomized spores of aerobic spore-forming *Bacillus* varieties in demineralised water was applied in the gap in a targeted way.

Not only was the required time reduced because the atomization could be done more quickly than vacuuming, but in addition an inspection 2 months later showed that the amount of accumulated dust in the gap was clearly lower in the part that had been cleaned with the method according to the invention, compared to the part that had been cleaned conventionally with a vacuum cleaner, such that this method according to the invention allows a lower and more effective cleaning frequency.

Another advantage of the method according to the invention is that it results in an electrostatic charge of the treated surface. In the known state of the art relating to the atomization of liquids a charge is formed on the droplets by the ballo-electrical effect (Thiago et al. J. Braz. Chem. Soc. Vol 27, No 2, AG 229-238, 2016). When aerosols are formed when atomizing a liquid with spores of bacteria, the droplets are given an equal electric charge and they mutually repel. In the event of sedimentation of the aerosols on dust, the charge of the aerosols is maintained, such that all the dust obtains one and the same charge and will repel other charged dust particles. The atomizer keeps the opposite charge.

An added advantage of the method according to the invention is that it stimulates the taking up and metabolising of dust by the germinated spores because the surface charge of *Bacillus* spores favourably affects their germination speed (Nishihara T. et al. Microbiol. Immunol. 1981; 25(8): 763-71). Spores of *Bacillus* varieties have a negative charge (Didouh N. et al., Afr. J. Microbiol. Res., Vol. 9 (2), AG 57-65, January 2015).

*Bacillus subtilis* spores survive being charged by electrospray treatment whereby the spores are desolvated and deagglomerated. (Pratt et al. J. Am. Soc. Mass Spectrom. 2014 May; 25(5):712-21, 2014 Feb. 25).

The advantages of the method for cleaning surfaces in interior spaces according to the invention can be summarised as follows:

- significant time savings (20-30%)
- lower cleaning frequency;
- significant reduction of visual dust deposit or dust burden by electrostatic repulsion;
- faster germination speed of the spores resulting in take-up and metabolising of dust;
- effective cleaning of all surfaces that are difficult to reach manually;
- elimination of the use of detergents and conventional cleaning products;
- minimising the amount of used water per surface unit when cleaning;
- increased safety (no danger of slipping);
- avoiding of shoe prints and streaks after cleaning;
- avoiding of finger prints with skin grease or deposits of cooking grease.

With the intention of better showing the characteristics of the invention, a preferred embodiment of the method to clean surfaces in interior spaces according to the invention is described hereinafter, by way of an example without any limiting nature, with reference to the accompanying drawings wherein:

FIG. 1 schematically shows a perspective view of an electric atomizer for use in the method for cleaning according to the invention;

FIG. 2 schematically shows the application of the targeted atomization of spores of benign bacteria on a surface of an interior space;

FIG. 3 schematically shows the optional take-up of the applied spores of benign bacteria by means of a microfibre;

Figure 1:
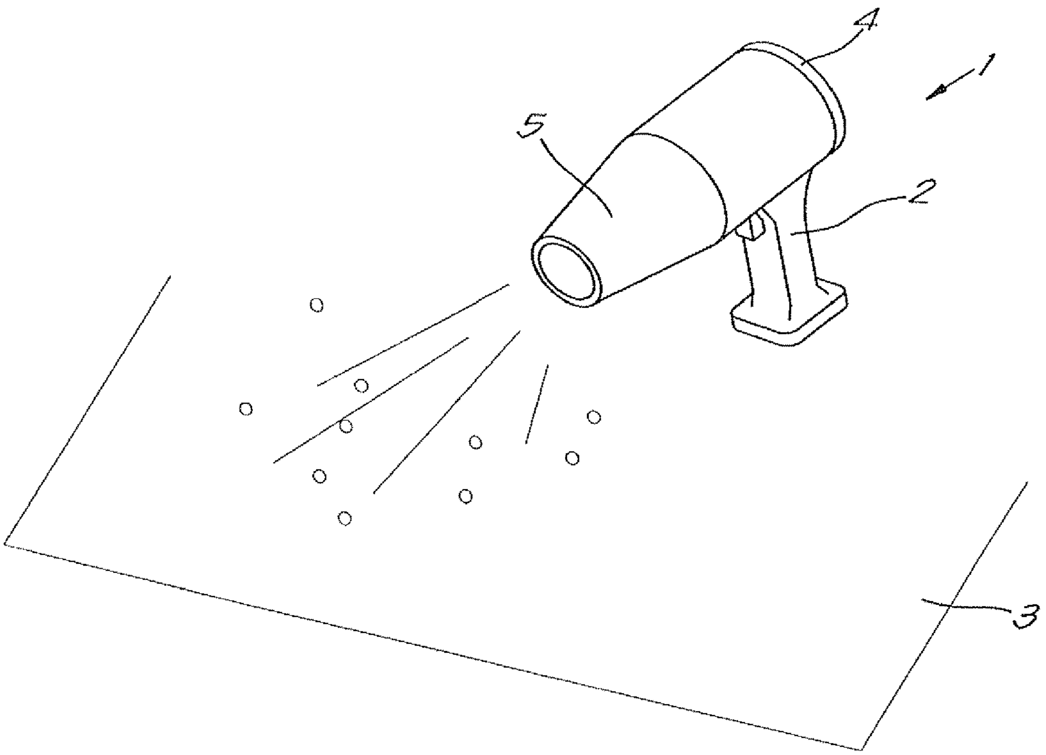

In FIG. 1 an atomizer 1 is shown for the targeted atomization of a liquid with spores of benign bacteria 2 on all or certain types of surfaces 3 in an interior space. The electric atomizer 1 consists of a fan 4 which can blow air through a solution of benign bacteria 2, and targets it via a nozzle 5 on a chosen surface.

Figure 2:
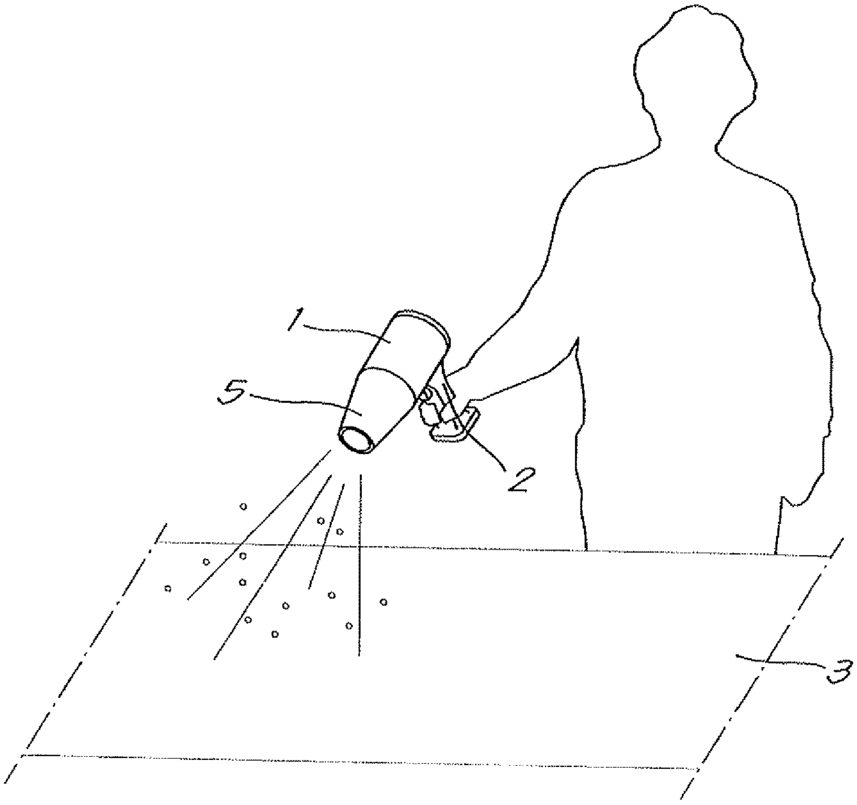

FIG. 2 schematically shows the application of the method for the cleaning of a surface in an interior space, consisting of a targeted atomization by means of an electric atomizer 1, in which a liquid with spores of benign bacteria 2 up to a droplet size of 80 μm is atomized, whereby in this case an aqueous solution of spores of benign bacteria of the genus *Bacillus* is dissolved.

Figure 3:
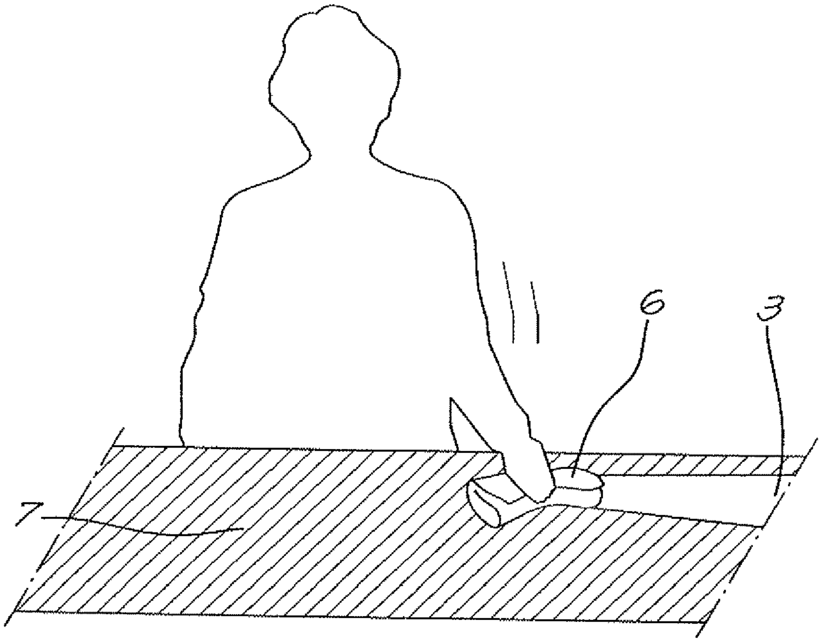

In FIG. 3 the use of a microfibre 6 to take up an atomized bacteria film 7 on a surface 3 is illustrated. The microfibre 6 can be wiped over the surface 3 that was sprayed to clean the surface 3 without the need to make it wet first.

Figure 4:
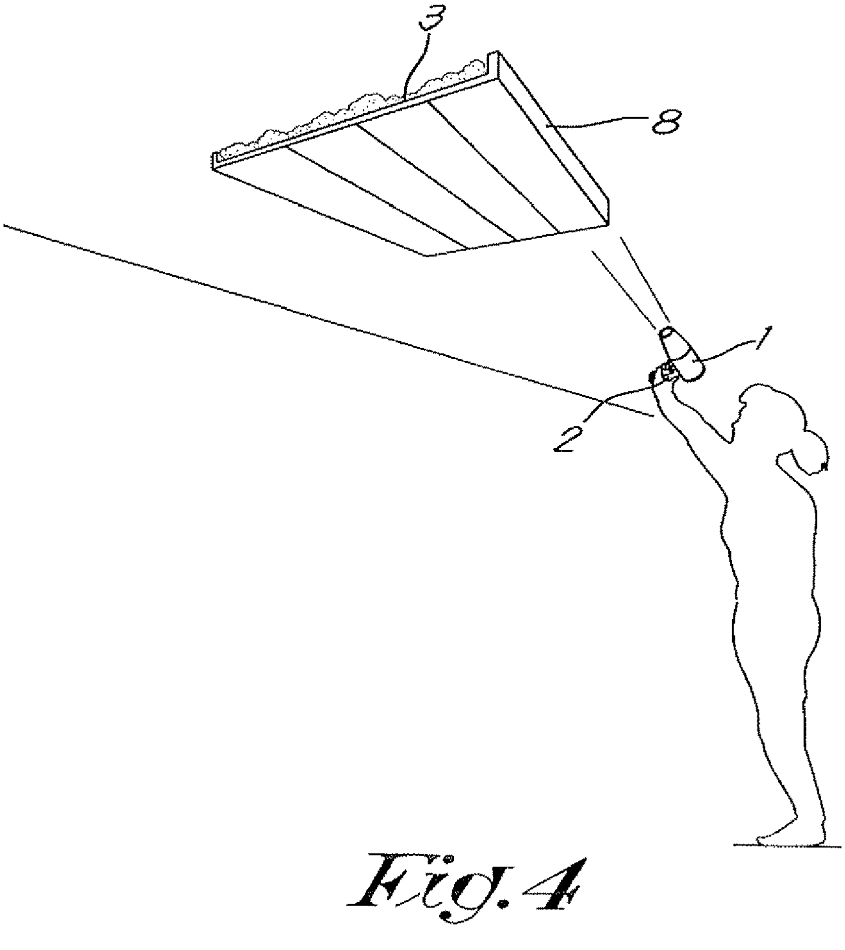
FIG. 4 shows the application on a climate ceiling of the method for cleaning according to the invention.

FIG. 4 shows the use of the method for the cleaning of a surface according to the invention, whereby in this case the surface 3 to be cleaned is a climate ceiling 8, which results in the cooling of an interior space. The distance between ceiling and climate ceiling is restricted, but can be cleaned by the targeted atomization of a solution with spores of benign bacteria possibly with 1% isopropyl-alcohol.

Figure 5:
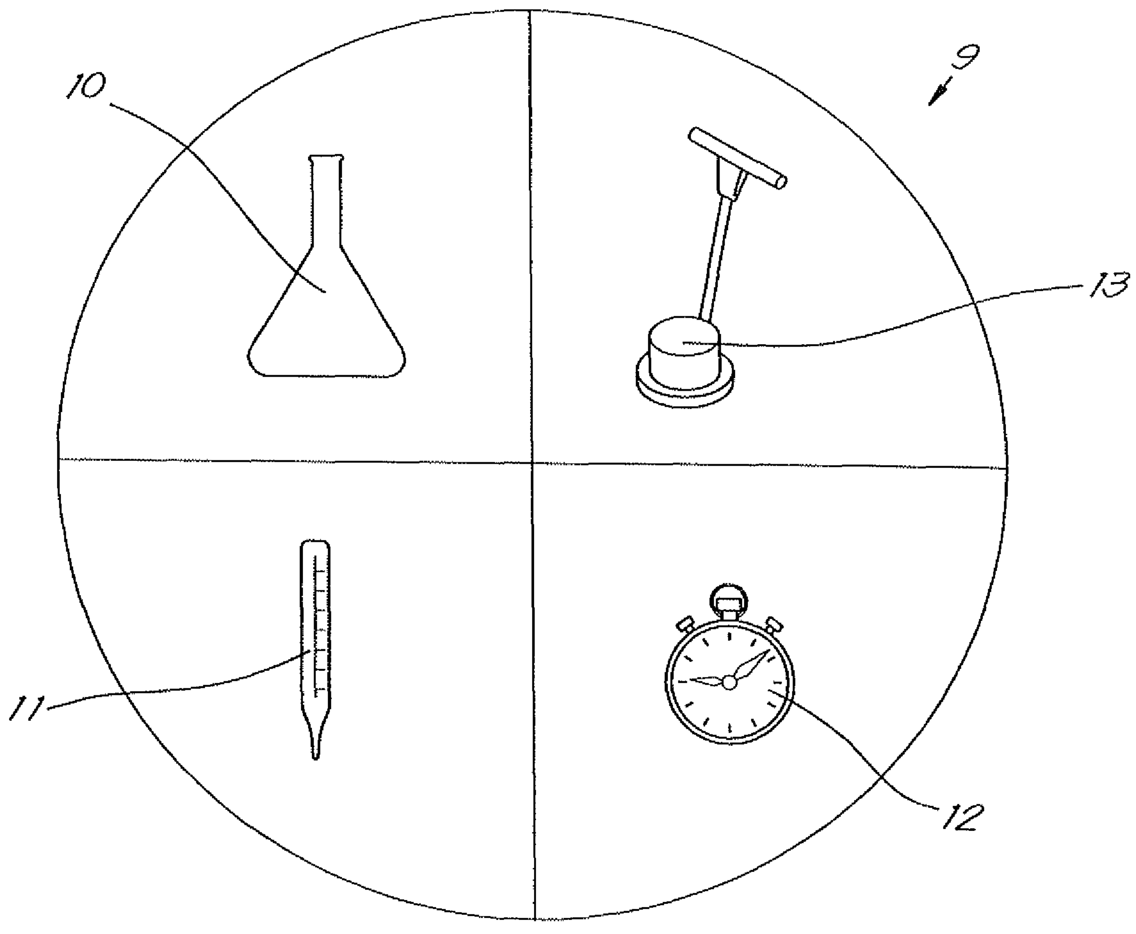
FIG. 5 shows a Sinner circle with the four factors that influence the cleaning.

FIG. 5 shows a Sinner circle 9 in which the four factors are presented which influence the cleaning. It concerns chemical cleaning products 10, the temperature 11 at which they are active, the time 12 during which they are active, and the mechanical treatment 13 with brushes or cloths required to clean a surface. Reduction of one of these factors must be compensated by increasing other factors to achieve the same result. Use of less strong chemicals will have to be compensated by allowing them to work over a longer period of time or at a higher temperature for example.

The present invention is by no means limited to the embodiments described as an example and shown in the figures, but such a method for the cleaning of surfaces in interior spaces can be realised according to different variants without departing from the scope of the invention, as described in the following claims.

The invention claimed is:

1. A method for lowering dust deposits on interior spaces or technical equipment, speeding up cleaning and lowering the frequency of cleaning of interior spaces or technical equipment, wherein said method consisting of:

targeting atomization of a liquid with spores of benign bacteria on a surface to be treated by means of an electrically and/or pneumatically powered atomizer, while said surface remains accessible to people and animals;

wherein droplets in aerosol formed by atomizing the liquid result in smaller than or equal to 80 μm in size and achieve the same electric charge in accordance with ballo-electrical effect, while also retaining said electric charge upon sedimentation of the aerosol on dust.

2. The method according to claim 1, wherein the concentration of spores of benign bacteria in the liquid to be atomized amounts to between $10^6$ KVE/ml and $50\times10^7$ KVE/ml.

3. The method according to claim 1, wherein the electric atomizer is an ultra-low volume atomizer, which generates a straight jet with a reach up to 15 metres or less.

4. The method according to claim 3, wherein the electric and/or pneumatic atomizer atomizes the liquid with spores of benign bacteria on the surface at a flow rate of maximum 300 ml a minute and an air flow of 0.2 litre per minute at a pressure of maximum 18 KPa.

5. The method according to claim 1, wherein the method is followed by manual or mechanical cleaning of the surface by means of a microfibre.

6. The method according to claim 1, wherein the amount of atomized liquid with spores of benign bacteria, applied per square metre of treated surface, amounts to maximum 10 grammes per $m^2$, with the purpose of not having the surface feel wet.

7. The method according to claim 6, wherein the spores of the benign bacteria in the atomized liquid are chosen from the genus *Bacillus* for applications at room temperature.

8. The method according to claim 7, wherein the benign bacteria in the atomized liquid chosen from the genus *Bacillus* consist of *Bacillus subtilis, Bacillus amyloliquefaciens, Bacillus pumilus, Bacillus licheniformis* or *Bacillus megaterium*, or a combination thereof.

9. The method according to claim 7, wherein the atomized liquid consists of a solution of spores of aerobic spore-forming *Bacillus* varieties dissolved in demineralised water with 1% isopropyl-alcohol.

10. The method according to claim 7, wherein said method stimulates the take-up and metabolising of dust by the germinated spores because the surface charge of *Bacillus* spores obtained by the ballo-electrical effect favourably influences their germination speed.

11. The method according to claim 6, wherein the spores of the benign bacteria in the atomized liquid are chosen from the spores of aerobic spore-forming cold-tolerant bacteria of the genera Sporosarcina, Paenisporosarcina or *Paenibacillus* or a combination thereof for applications at cold environmental temperatures between 4 and 18° c.

12. The method according to claim 11, wherein the spores of the benign bacteria in the atomized liquid chosen from the genus Sporosarcina consist of Sporosarcina globispora, *aquimarina*, or psychrophile, or a combination thereof.

13. The method according to claim 11, wherein the spores of benign bacteria in the atomized liquid chosen from the genus Paenisporosarcina consist of the spores of Paenisporosarcina macmoerdoensis.

14. The method according to claim 11, wherein the spores of benign bacteria in the atomized liquid chosen from the genus *Paenibacillus* consist of the spores of *Paenibacillus glacialis, amylolyticus, pabuli*, xylanexedens, castaneae, or *macquariensis antarcticus* or a combination thereof.

15. The method according to claim 1, wherein the method is used to clean spaces that are difficult to reach for manual cleaning.

* * * * *